US 8,894,565 B2

(12) United States Patent
Naito

(10) Patent No.: US 8,894,565 B2
(45) Date of Patent: Nov. 25, 2014

(54) INSERTION DEVICE, ROTATING TUBULAR MEMBER, AND DRIVING UNIT

(71) Applicant: Olympus Medical Systems Corp., Tokyo (JP)

(72) Inventor: Kimihiko Naito, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/016,598

(22) Filed: Sep. 3, 2013

(65) Prior Publication Data

US 2014/0066713 A1    Mar. 6, 2014

Related U.S. Application Data

(63) Continuation of application No. PCT/JP2013/050384, filed on Jan. 11, 2013.

(30) Foreign Application Priority Data

Mar. 30, 2012    (JP) .................................. 2012-082746

(51) Int. Cl.
*A61B 1/00*    (2006.01)
*A61B 1/06*    (2006.01)
*G02B 23/24*    (2006.01)

(52) U.S. Cl.
CPC ........... *A61B 1/0016* (2013.01); *A61B 1/00156* (2013.01); *A61B 1/0669* (2013.01); *A61B 1/00009* (2013.01); *A61B 1/00117* (2013.01); *G02B 23/2476* (2013.01); *A61B 1/00045* (2013.01); *A61B 1/00158* (2013.01); *A61B 1/00154* (2013.01)
USPC ........... 600/114; 600/128; 600/129; 600/137; 600/173; 600/174

(58) Field of Classification Search
CPC ........... A61B 1/00133; A61B 1/00147; A61B 1/00151; A61B 1/0016; A61B 1/0057
USPC .................. 600/114, 128, 129, 137, 173–174
See application file for complete search history.

(56) References Cited

U.S. PATENT DOCUMENTS 8,500,628 B2 *   8/2013   Frassica et al. ................ 600/114
2005/0177026 A1 *   8/2005   Hoeg et al. ..................... 600/173
(Continued)

FOREIGN PATENT DOCUMENTS

JP    2005-253892 A    9/2005
JP    2007-185394 A    7/2007
(Continued)

OTHER PUBLICATIONS

International Search Report from related International Application No. PCT/JP2013/050384, dated Feb. 5, 2013.

*Primary Examiner* — Matthew J Kasztejna
*Assistant Examiner* — Kevin G Barry, III
(74) *Attorney, Agent, or Firm* — Scully, Scott, Murphy & Presser, PC

(57)    ABSTRACT

An insertion device includes a channel defining portion extended through an inside of an insertion section up to a base portion toward a distal direction and defining a channel that is open to an outside of the insertion section in an opening of an outer peripheral portion of the base portion, and a driving unit extended through an inside of the channel with a driving axis being an axial center and being rotatable in directions around the driving axis when driven. The insertion device includes a driving force receiving portion connected to a gear portion in the opening of the channel, and a support unit supporting the driving unit so that the driving axis is parallel to the longitudinal axis in the gear portion.

6 Claims, 10 Drawing Sheets

(56) References Cited

U.S. PATENT DOCUMENTS

| | | | |
|---|---|---|---|
| 2005/0256507 A1* | 11/2005 | Long et al. | 604/528 |
| 2007/0167684 A1* | 7/2007 | Toyama | 600/114 |
| 2010/0063361 A1* | 3/2010 | Kuchimaru et al. | 600/168 |
| 2012/0002981 A1 | 1/2012 | Park | |
| 2013/0102848 A1* | 4/2013 | Moriyama | 600/114 |

FOREIGN PATENT DOCUMENTS

| | | |
|---|---|---|
| JP | 2009-501555 A | 1/2009 |
| JP | 2009-189653 A | 8/2009 |

\* cited by examiner

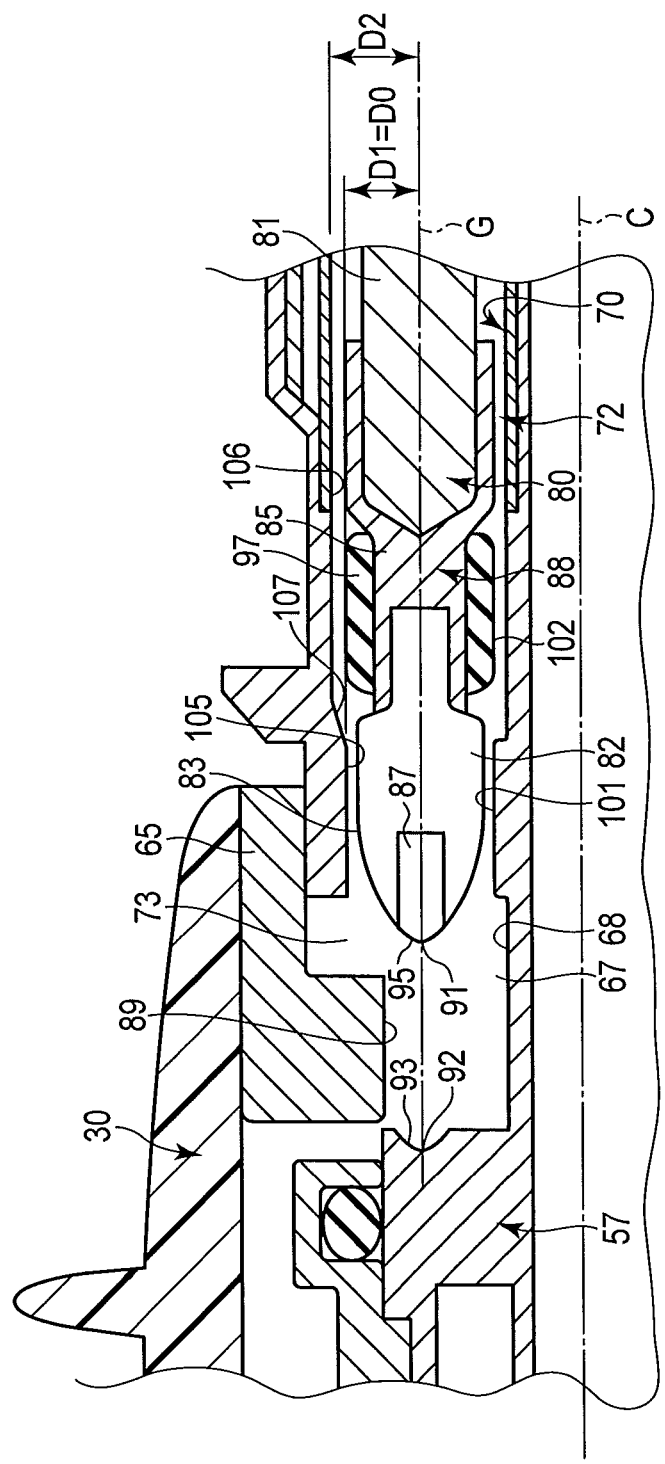
F I G. 7

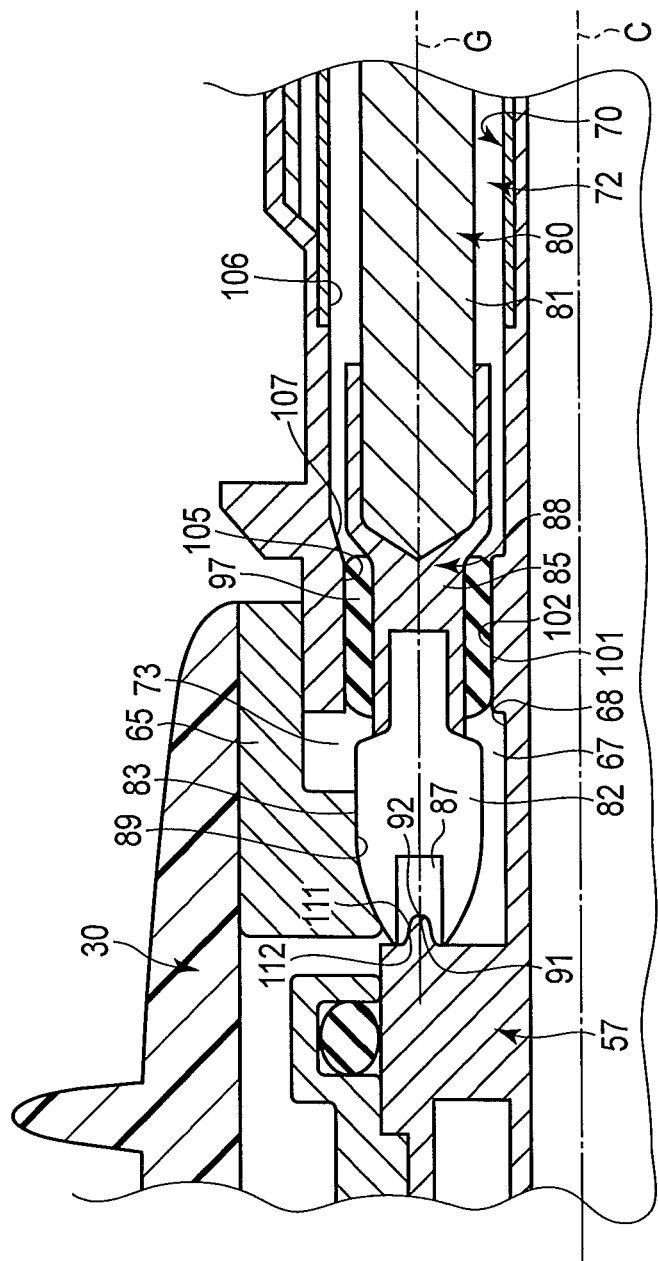
F I G. 8

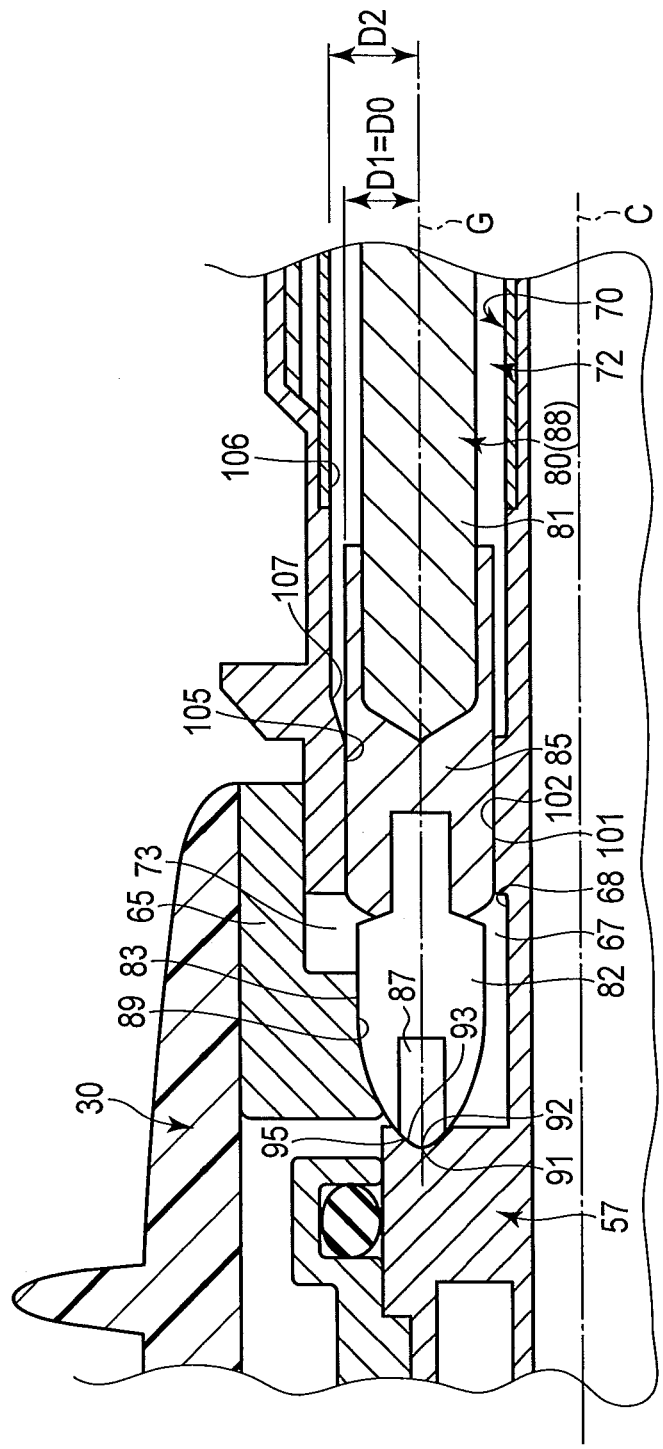
F I G. 9A

INSERTION DEVICE, ROTATING TUBULAR MEMBER, AND DRIVING UNIT

CROSS-REFERENCE TO RELATED APPLICATIONS

This is a Continuation Application of PCT Application No. PCT/JP2013/050384, filed Jan. 11, 2013 and based upon and claiming the benefit of priority from prior Japanese Patent Application No. 2012-082746, filed Mar. 30, 2012, the entire contents of which are incorporated herein by reference.

BACKGROUND OF THE INVENTION

1. Field of the Invention

The present invention relates to an insertion device, a rotating tubular member, and a driving unit. The insertion device includes an insertion section extended along a longitudinal axis, and the rotating tubular member which is rotatable relative to the insertion section in directions around the longitudinal axis. The rotating tubular member is provided to (in) the insertion device. The driving unit is configured to transmit a rotation driving force to rotate the rotating tubular member.

2. Description of the Related Art

In an insertion device disclosed by way of example in the specification of U.S. Patent Application Publication No. 2012/002981, a rotating tubular member rotatable relative to an insertion section in directions around a longitudinal axis is attached to the insertion section extended along the longitudinal axis. In this insertion device, the rotating tubular member is attached to a base portion of the insertion section. A member channel is extended through an inside of the insertion section up to the base portion toward a distal direction. The member channel is open to an outside of the insertion section in an opening of an outer peripheral portion of the base portion. A driving unit is extended through the member channel with a driving axis being an axial center. The driving unit includes a driving shaft, which is a linear member, extended along the driving axis, and a gear portion provided to the distal direction side of the driving shaft. The driving unit is driven and thereby rotates in one of directions around the driving axis. The rotating tubular member is provided with an inner peripheral gear portion which is a driving force receiving portion. The inner peripheral gear portion is toothed with a gear portion in the opening of the member channel. The driving unit is driven, and the gear portion rotates in one of the directions around the driving axis, so that the rotating tubular member rotates relative to the insertion portion in one of the directions around the longitudinal axis.

The driving unit includes a supported portion provided to the distal direction side of the gear portion. A support portion which supports the supported portion is provided to the base portion. The support portion supports the supported portion so that the driving unit is rotatable in the directions around the driving axis.

BRIEF SUMMARY OF THE INVENTION

According to one aspect of the invention, an insertion device includes that an insertion section extended along a longitudinal axis with the longitudinal axis being an axial center; a rotating tubular member which is attached to the insertion section so that the insertion section is inserted through the rotating tubular member, and which is rotatable relative to the insertion section in directions around the longitudinal axis; a base portion which is provided to the insertion section, and to which the rotating tubular member is rotatably attached; a channel defining portion which extended through an inside of the insertion section up to the base portion toward a distal direction, and which defines a channel that is open to an outside of the insertion section in an opening of an outer peripheral portion of the base portion; a driving unit which is extended through an inside of the channel with a driving axis being an axial center, and which is rotatable in directions around the driving axis when driven, the driving unit including a linear member extended along the driving axis, and a gear portion which is provided to the distal direction side of the linear member and to which a driving force is configured to be transmitted via the linear member; a driving force receiving portion which is provided to the rotating tubular member, and to which a rotation driving force to rotate the rotating tubular member is configured to be transmitted when the gear portion is driven, the driving force receiving portion being connected to the gear portion in the opening of the channel; and a support unit which is configured to support the driving unit so that the driving axis is parallel to the longitudinal axis in the gear portion.

According to one another aspect of the invention, a rotating tubular member in an insertion device, the insertion device including an insertion portion which is extended along a longitudinal axis with the longitudinal axis being an axial center and which includes a base portion, a channel defining portion which is extended through an inside of the insertion section up to the base portion toward a distal direction and which defines a channel that is open to an outside of the insertion section in an opening of an outer peripheral portion of the base portion, and a driving unit which is extended through an inside of the channel with a driving axis being an axial center and which is rotatable in directions around the driving axis when driven, the driving unit including a linear member extended along the driving axis, and a gear portion which is provided to the distal direction side of the linear member and to which a driving force is configured to be transmitted via the linear member, the rotating tubular member being attached to the base portion of the insertion section so that the insertion section is inserted through the rotating tubular member, the rotating tubular member being rotatable relative to the insertion section in directions around the longitudinal axis, the rotating tubular member including a driving force receiving portion to which a rotation driving force to rotate the rotating tubular member is configured to be transmitted when the gear portion is driven, the driving force receiving portion being connected to the gear portion in the opening of the channel, wherein the rotation driving force is configured to be transmitted to the rotating tubular member via the driving unit which is supported so that the driving axis is parallel to the longitudinal axis in the gear portion.

Further, according to one another aspect of the invention, a driving unit in an insertion device, the insertion device including an insertion section which is extended along a longitudinal axis with the longitudinal axis being an axial center and which includes a base portion, a rotating tubular member which is attached to the base portion of the insertion section so that the insertion section is inserted through the rotating tubular member and which is rotatable relative to the insertion section in directions around the longitudinal axis, and a channel defining portion which is extended through an inside of the insertion section up to the base portion toward a distal direction and which defines a channel that is open to an outside of the insertion section in an opening of the outer peripheral portion of the base portion, the driving unit being extended through an inside of the channel with a driving axis being an axial center and which is rotatable in directions around the driving axis when driven, the driving unit comprising a linear member extended along the driving axis, and a gear portion which is provided to the distal direction side of the linear member and to which a driving force is configured to be transmitted via the linear member, wherein the gear portion is configured to be driven and thereby configured to transmit a rotation driving force to rotate the rotating tubular member to a driving force receiving portion of the rotating tubular member, and the gear portion is connected to the driving force receiving portion in the opening of the channel, and the driving unit is configured to be supported so that the driving axis is parallel to the longitudinal axis in the gear portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 7 is a schematic sectional view showing a state in which a proximal supported portion of a driving unit passes through an inside of a second channel diameter setting portion of a channel defining portion during the movement of the driving unit through a member channel according to the first embodiment;

FIG. 8 is a schematic sectional view showing the configuration of a part of a second intermediary connection section in the vicinity of a gear placement cavity according to a first modification;

FIG. 9A is a schematic sectional view showing the configuration of a part of a second intermediary connection section in the vicinity of a gear placement cavity according to a second modification;

DETAILED DESCRIPTION OF THE INVENTION

First Embodiment

Figure 1:
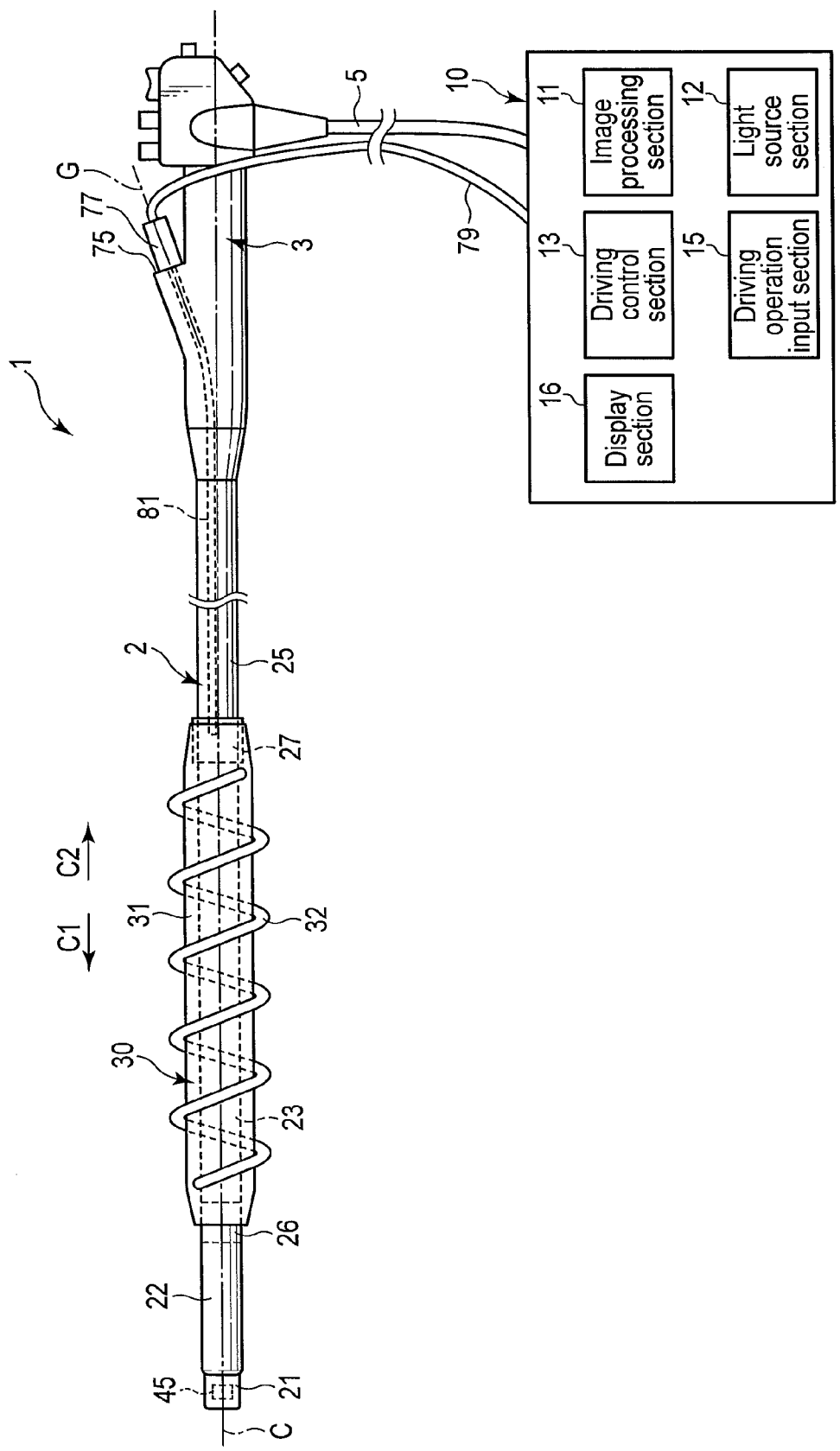
FIG. 1 is a schematic diagram showing an endoscope device according to a first embodiment.

A first embodiment of the present invention is described with reference to FIG. 1 to FIG. 7. FIG. 1 is a diagram showing an endoscope device 1 which is an insertion device according to the first embodiment. As shown in FIG. 1, the endoscope device 1 includes an insertion section (endoscope insertion section) 2 extended along a longitudinal axis C, and an operation section (endoscope operation section) 3 provided to a proximal direction side of the insertion section 2. The longitudinal axis C is an axial center in the insertion section 2, and the insertion section 2 is configured to be inserted into a body cavity when the endoscope device 1 is used. One end of a universal cable 5 is connected to the operation section 3. The other end of the universal cable 5 is connected to a peripheral unit 10. The peripheral unit 10 includes an image processing section 11, a light source section 12, a driving control section 13, a driving operation input section 15, and a display section 16. It is to be noted that one of directions parallel to the longitudinal axis C is a distal direction (direction of an arrow C1 in FIG. 1), and the direction opposite to the distal direction is the proximal direction (direction of an arrow C2 in FIG. 1).

The insertion section 2 includes a distal rigid section 21 provided to the most-distal side in the insertion section 2, a bending section 22 provided to the proximal direction side of the distal rigid section 21, a first flexible tube section 23 provided to the proximal direction side of the bending section 22, and a second flexible tube section 25 provided to the proximal direction side of the first flexible tube section 23. The bending section 22 and the first flexible tube section 23 are connected by a first intermediary connection section 26. The first flexible tube section 23 and the second flexible tube section 25 are connected by a second intermediary connection section 27.

A tube member 30 is provided to an outer peripheral direction side of the insertion section 2. The insertion section 2 is inserted through the tube member 30. The tube member 30 is extended along the longitudinal axis C between the first intermediary connection section 26 and the second intermediary connection section 27. The tube member 30 is rotatable relative to the insertion section 2 in directions around the longitudinal axis C. The tube member 30 includes a tube body 31, and a fin 32 spirally extended on an outer peripheral portion of the tube body 31 along the longitudinal axis C.

Figure 2:
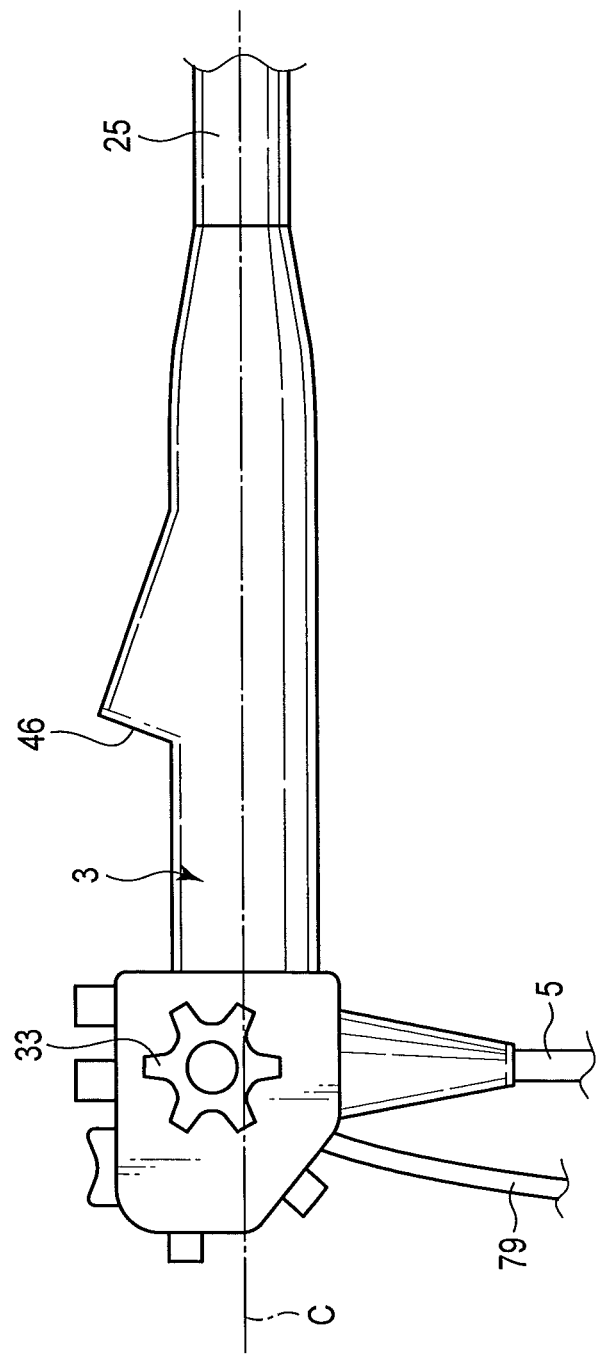
FIG. 2 is a schematic diagram showing a side surface of an operation section of the endoscope device according to the first embodiment opposite to a side surface shown in FIG. 1.
Figure 3:
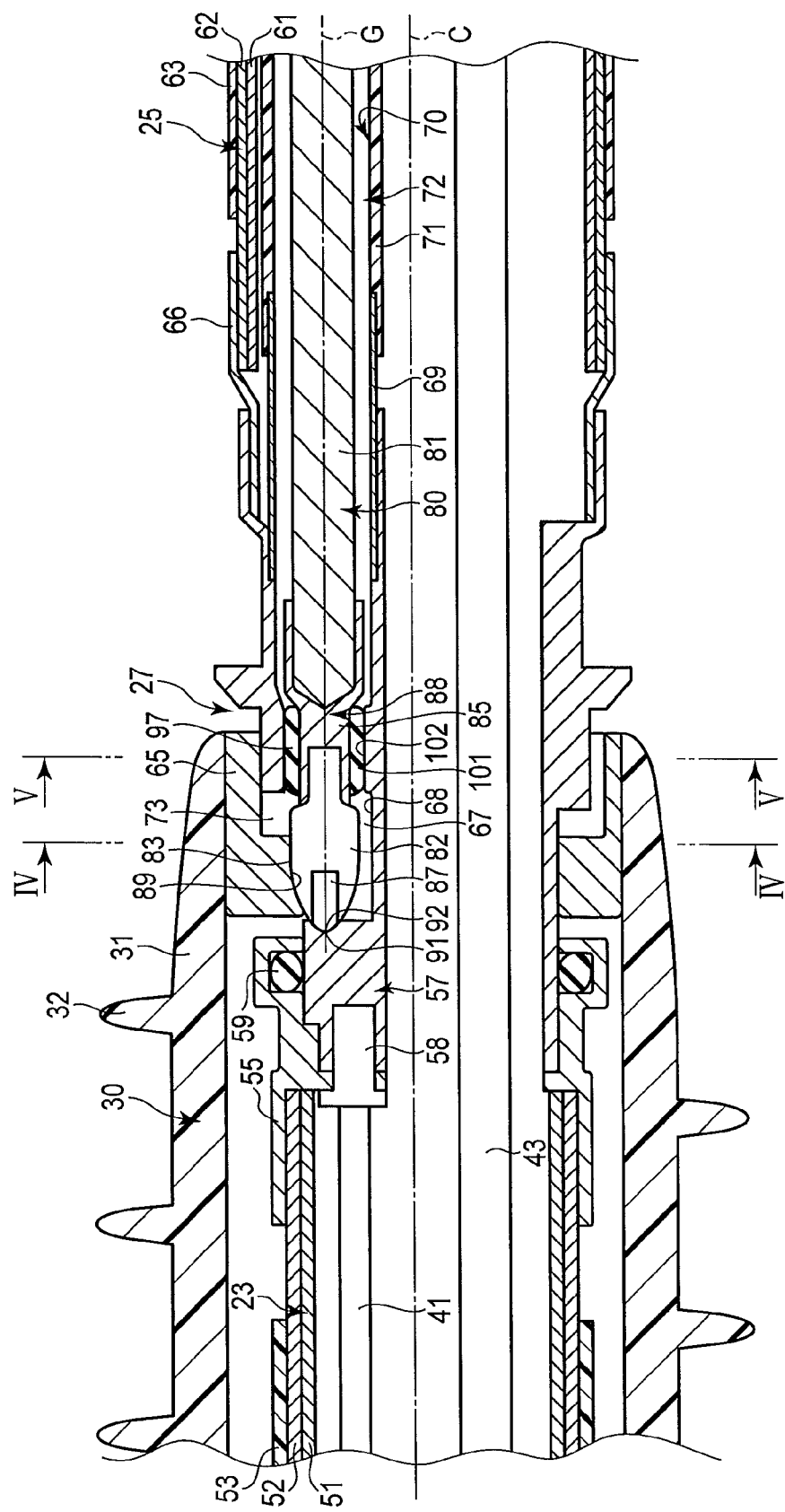
FIG. 3 is a schematic sectional view showing the configuration of a second intermediary connection section of an insertion section according to the first embodiment.
Figure 4:
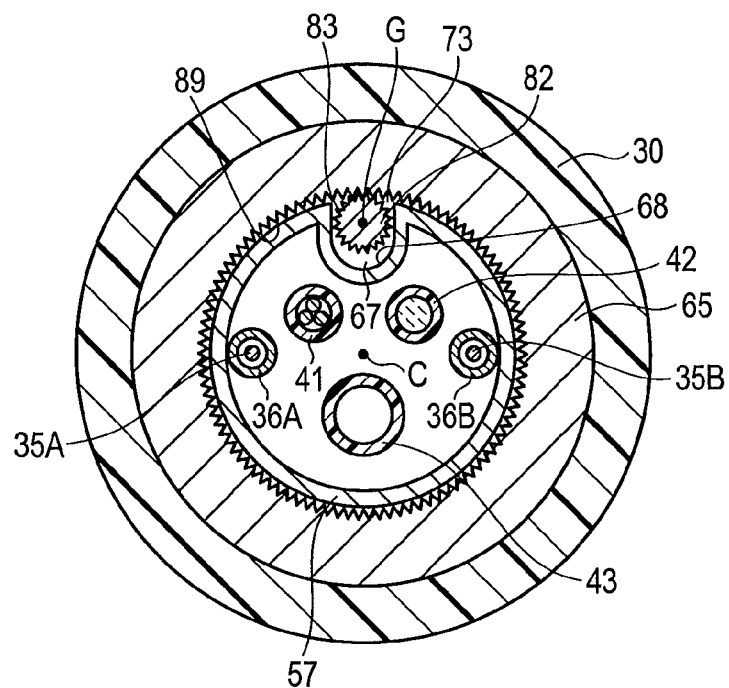
FIG. 4 is a sectional view taken along the line IV-IV in FIG. 3.
Figure 5:
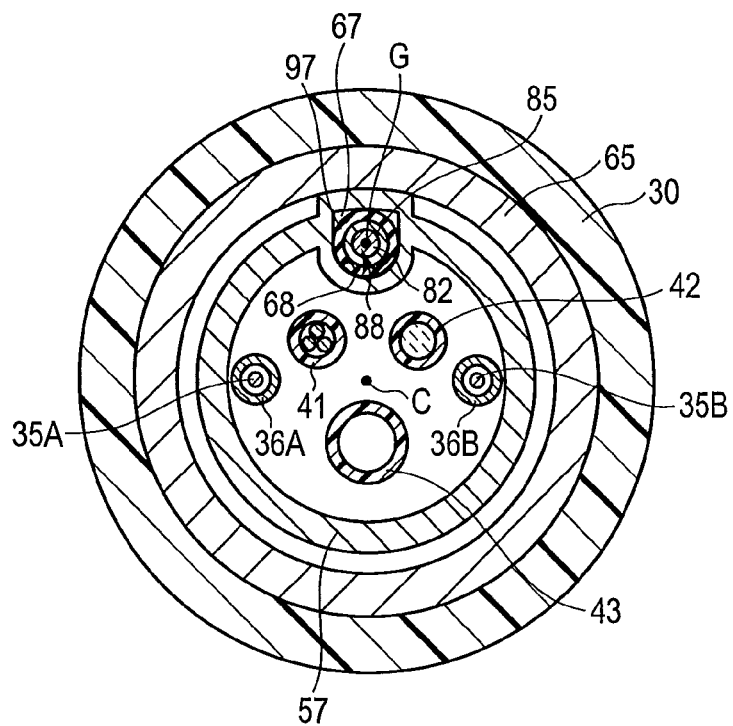
FIG. 5 is a sectional view taken along the line V-V in FIG. 3.

FIG. 2 is a diagram showing a side surface of the operation section 3 opposite to a side surface shown in FIG. 1. As shown in FIG. 2, a bending operation knob 33, which is a bending operation input portion to input a bending operation of the bending section 22, is provided on an outer surface of the operation section 3. FIG. 3 is a diagram showing the configuration of the second intermediary connection section 27. FIG. 4 is a sectional view taken along the line IV-IV in FIG. 3. FIG. 5 is a sectional view taken along the line V-V in FIG. 3. As shown in FIG. 4 and FIG. 5, bending wires 35A and 35B extend through an inside of the insertion section 2 along the longitudinal axis C. Proximal ends of the bending wires 35A and 35B are connected to the bending operation knob 33 inside the operation section 3. Distal ends of the bending wires 35A and 35B are connected to a distal end portion of the bending section 22. In response to the bending operation of the bending operation knob 33, the bending wire 35A or the bending wire 35B is pulled, and the bending section 22 bends.

Each of the bending wires 35A and 35B is inserted through a corresponding coil 36A or 36B. Proximal ends of the coils 36A and 36B are connected to an inner peripheral portion of the operation section 3. Distal ends of the coils 36A and 36B are connected to an inner peripheral portion of the first intermediary connection section 26. In the present embodiment, the two bending wires 35A and 35B are provided, and the bending section 22 is bendable in two directions. However, for example, four bending wires may be provided, and the bending section 22 may be bendable in four directions.

As shown in FIG. 3 to FIG. 5, an imaging cable 41, a light guide 42, and a treatment tool channel tube 43 are extended through the inside of the insertion section 2 along the longitudinal axis C. As shown in FIG. 1, an image pickup element 45 configured to imaging a subject is provided inside the distal rigid section 21 (a distal end portion of the insertion section 2). A distal end of the imaging cable 41 is connected to the image pickup element 45. The imaging cable 41 is extended through the inside of the insertion section 2, the inside of the operation section 3, and an inside the universal cable 5, and has its proximal end connected to the image processing section 11 of the peripheral unit 10. A subject image processed by the image processing section 11 is displayed on the display section 16. The light guide 42 is extended through the inside of the insertion section 2, the inside of the operation section 3, and the inside of the universal cable 5, and has its proximal end connected to the light source section 12 of the peripheral unit 10. Light emitted from the light source section 12 is guided by the light guide 42, and applied to the subject from the distal end portion (distal rigid section 21) of the insertion section 2.

As shown in FIG. 2, a treatment tool insertion portion 46 through which a treatment tool such as a forceps is inserted is provided on the outer surface of the operation section 3. The treatment tool channel tube 43 has its proximal end connected to the treatment tool insertion portion 46, and extended through the inside of the insertion section 2 and the inside of the operation section 3. The treatment tool inserted from the treatment tool insertion portion 46 projects toward the distal direction from an opening (not shown) of the distal rigid section 21 through the treatment tool channel tube 43. A treatment is then conducted by the treatment tool so that the treatment tool projects from the opening of the distal rigid section 21.

As shown in FIG. 3, a metallic first helical tube (first flex) 51 is provided to (in) the first flexible tube section 23. The first helical tube 51 is covered with a metallic first flexible reticular tube (first flexible braid) 52 from the outer peripheral direction side. The first flexible reticular tube 52 is covered with a resin first flexible envelope 53 from the outer peripheral direction side. The proximal ends of the first helical tube 51 and the first flexible reticular tube 52 are fitted in an intermediary member 55. The second intermediary connection section 27 includes a metallic base member 57. The intermediary member 55 is fitted in the base member 57 via a ring member 59. The intermediary member 55 is attached to the base member 57 via a screw 58. In this way, the first flexible tube section 23 is coupled to the second intermediary connection section 27.

A metallic second helical tube (second flex) 61 is provided to (in) the second flexible tube section 25. The second helical tube 61 is covered with a metallic second flexible reticular tube (second flexible braid) 62 from the outer peripheral direction side. The second flexible reticular tube 62 is covered with a resin second flexible envelope 63 from the outer peripheral direction side. The distal end of the second helical tube 61 and the distal end of the second flexible reticular tube 62 are fitted in an intermediary member 66. The intermediary member 66 is fitted in the base member 57. In this way, the second flexible tube section 25 is coupled to the second intermediary connection section 27.

A rotating tubular member 65 is attached to the second intermediary connection section 27 of the insertion section 2 in a state that the insertion section 2 is inserted through the rotating tubular member 65. The rotating tubular member 65 is rotatable relative to the insertion section 2 in the directions around the longitudinal axis. That is, the base member 57 serves as a base portion to which the rotating tubular member 65 is rotatably attached. The proximal end portion of the tube member 30 is in close contact with an outer peripheral portion of the rotating tubular member 65. Thus, the tube member 30 is fixed to the rotating tubular member 65, and the tube member 30 is rotatable in the directions around the longitudinal axis together with the rotating tubular member 65. The distal end portion of the tube member 30 is in contact with an outer peripheral portion of the first intermediary connection section 26 with being movably relative to the insertion section 2 in the directions around the longitudinal axis.

As shown in FIG. 3, a cavity defining portion 68 which defines a gear placement cavity 67 is provided to (in) the base member 57 (base portion). A metallic connection pipe 69 is fixed to the cavity defining portion 68 of the base member 57. A distal end of a member channel tube 71 is connected to the connection pipe 69. The member channel tube 71 is extended through an inside of the second flexible tube section 25 of the insertion section 2 along the longitudinal axis C. A member channel 72 is formed in the connection pipe 69 and the member channel tube 71. The gear placement cavity 67 is located at a distal end portion of the member channel 72, and is a part of the member channel 72. That is, the member channel 72 is extended through the inside of the insertion section 2 up to the base member 57 (base portion) toward the distal direction. The member channel 72 is open to an outside of the insertion section 2 in an opening 73 of an outer peripheral portion of the base member 57. Here, the cavity defining portion 68 of the base member 57, the connection pipe 69, and the member channel tube 71 serve as a channel defining portion 70 which defines the member channel 72.

As shown in FIG. 1, a member insertion portion 75 is provided on the outer surface of the operation section 3. The member channel tube 71 has its proximal end connected to the member insertion portion 75, and is extended through the inside of the second flexible tube section 25 and the inside of the operation section 3. Therefore, the member channel 72 is extended from the member insertion portion 75 up to the opening 73 of the base member 57 through the inside of the member channel tube 71.

A motor 77 which is a driving member is attached to the member insertion portion 75. One end of a motor cable 79 is connected to the motor 77. The other end of the motor cable 79 is connected to the driving control section 13 of the peripheral unit 10.

As shown in FIG. 3 to FIG. 5, a driving unit 80 is extended through the member channel 72. The driving unit 80 is driven with a driving axis G being an axial center, and is thereby rotatable in directions around the driving axis. The driving unit 80 includes a driving shaft 81, which is a linear member, extended along the driving axis G, a driving gear 82 provided to the distal direction side of the driving shaft 81. A gear portion 83 is provided on an outer peripheral portion of the driving gear 82 over the all-round of the driving gear 82 in the directions around the driving axis. The driving shaft 81 is coupled to the driving gear 82 via a connection member 85. A proximal end of the driving shaft 81 is connected to the motor 77. A columnar member 87 is provided to the distal direction side of the driving gear 82 and fixed to the driving gear 82.

A driving body 88 is constituted by the driving shaft 81, the driving gear 82, the connection member 85, and the columnar member 87. That is, the gear portion 83 is provided to (in) the driving body 88. Therefore, the driving body 88 is rotatable in the directions around the driving axis together with the gear portion 83.

If the motor 77 is driven by an operation in the driving operation input section 15, the driving unit 80 including the driving shaft 81 and the driving gear 82 rotates in one of the directions around the driving axis. As a result, the gear portion 83 moves in one of the directions around the driving axis. That is, if the motor 77 is driven, the driving force is transmitted to the gear portion 83 via the driving shaft 81, and the gear portion 83 is driven.

An inner peripheral gear portion 89 which is toothed with the gear portion 83 of the driving gear 82 is provided on the inner peripheral portion of the rotating tubular member 65. The inner peripheral gear portion 89 is provided over the all-round of the rotating tubular member 65 in the directions around the longitudinal axis. Thus, when the gear portion 83 rotates around the driving axis G, the rotating tubular member 65 rotates in one of the directions around the longitudinal axis. That is, the inner peripheral gear portion 89 is a driving force receiving portion to which the rotation driving force to rotate the rotating tubular member 65 is transmitted when the inner peripheral gear portion 89 is connected to the gear portion 83 of the driving unit 80 and then the driving unit 80 is driven. The gear portion 83 and the inner peripheral gear portion 89 are toothed with each other at the opening 73 of the member channel 72.

Figure 6:
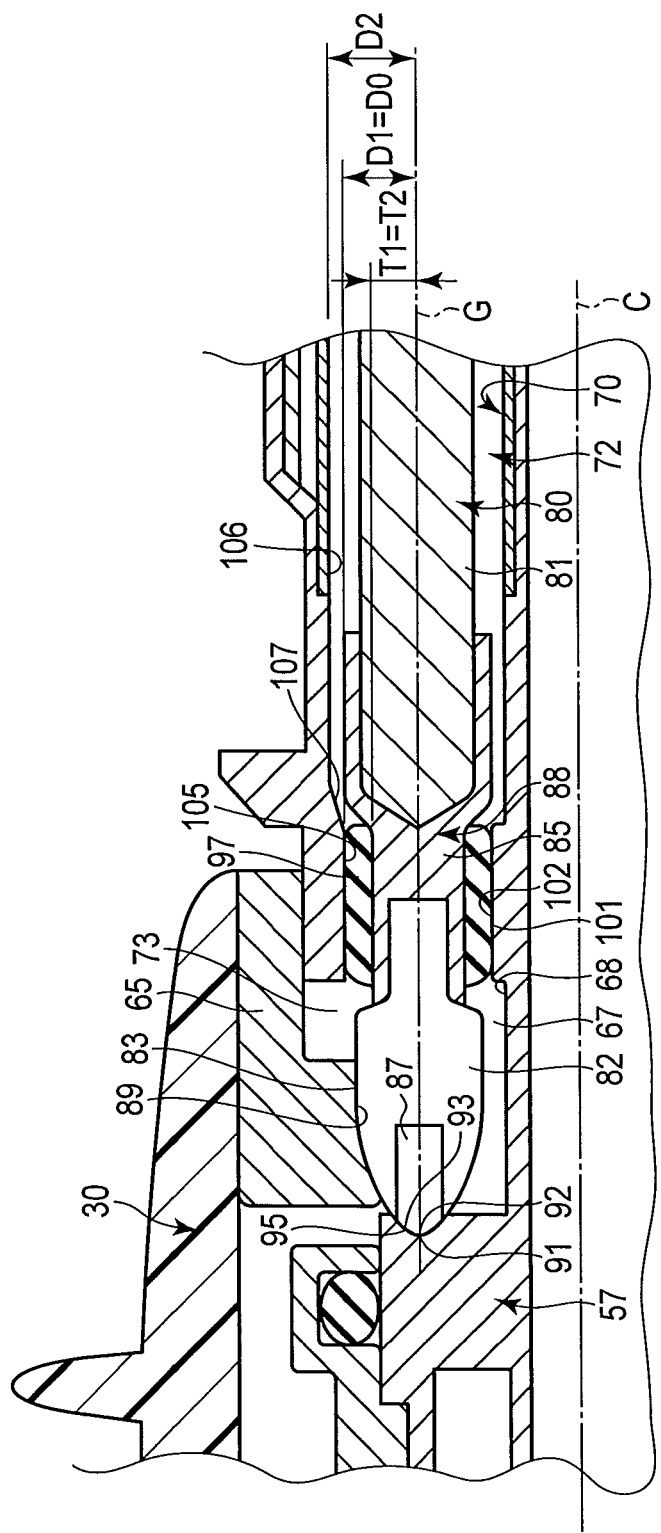
FIG. 6 is a schematic sectional view showing the configuration of a part of the second intermediary connection section in the vicinity of a gear placement cavity according to the first embodiment.

FIG. 6 is a diagram showing the configuration of a part in the vicinity of the gear placement cavity 67. As shown in FIG. 6, a distal supported portion 91 is provided to (in) the columnar member 87 of the driving unit 80. The distal supported portion 91 is located to the distal direction side of the gear portion 83. A distal support portion 92 which is configured to support the distal supported portion 91 is provided to (in) the cavity defining portion 68 (channel defining portion 70) of the base member 57 (base portion). The driving axis G of the driving unit 80 passes through the distal supported portion 91 and the distal support portion 92.

An insertion section side taper surface 93 is provided to (in) the cavity defining portion 68 (channel defining portion 70) of the base member 57 from the distal support portion 92 toward the proximal direction. In the insertion section side taper surface 93, a dimension from the driving axis G in a section perpendicular to the driving axis G is increased as it goes toward the proximal direction. A driving side taper surface 95 is provided to (in) the columnar member 87 of the driving unit 80 from the distal supported portion 91 toward the proximal direction. In the driving side taper surface 95, a dimension from the driving axis G in the section perpendicular to the driving axis G is increased as it goes toward the proximal direction. In such a configuration, the distal supported portion 91 of the driving unit 80 is guided to the distal support portion 92 of the cavity defining portion 68 (channel defining portion 70) by the insertion section side taper surface 93. That is, the insertion section side taper surface 93 is a distal guide portion which can (configured to) guide the driving unit 80 so that the distal supported portion 91 is supported by the distal support portion 92.

On an outer peripheral portion of the connection member 85 of the driving body 88, a ring member 97 is provided as a part of the driving unit 80. The driving body 88 is inserted through the ring member 97. The ring member 97 is rotatable relative to the driving body 88 in the directions around the driving axis. A proximal supported portion 101 is provided on (in) an outer peripheral portion of the ring member 97. That is, the proximal supported portion 101 is provided on (in) the outer peripheral portion of the driving unit 80. The proximal supported portion 101 is located to the proximal direction side of the gear portion 83. A proximal support portion 102 which is configured to support the proximal supported portion 101 is provided to (in) the cavity defining portion 68 (channel defining portion 70) of the base member 57 (base portion).

In the present embodiment, the driving unit 80 is supported by the distal supported portion 91 located to the distal direction side of the gear portion 83 and by the proximal supported portion 101 located to the proximal direction side of the gear portion 83. As a result, the driving unit 80 is supported by the distal support portion 92 and the proximal support portion 102 so that the driving axis G is parallel to the longitudinal axis C in the gear portion 83. That is, the distal support portion 92 and the proximal support portion 102 serve as a support unit which is configured to support the driving unit 80 so that the driving axis G is parallel to the longitudinal axis C in the gear portion 83.

As shown in FIG. 6, a first channel diameter setting portion 105 in which a channel diameter dimension from the driving axis G is a first channel diameter dimension D1 is provided to (in) the cavity defining portion 68 of the channel defining portion 70. The proximal support portion 102 is provided to (in) the first channel diameter setting portion 105. In the section perpendicular to the driving axis G which passes through the proximal supported portion 101 of the ring member 97 of the driving unit 80, the driving unit 80 has a driving unit diameter dimension D0 from the driving axis G to the proximal supported portion 101. The driving unit diameter dimension D0 is the same as the first channel diameter dimension D1 in the first channel diameter setting portion 105.

In the section perpendicular to the driving axis G, a first member diameter dimension T1 from the driving axis G to the outer peripheral portion of the connection member 85 of the driving body 88 is substantially the same as a second member diameter dimension T2 from the driving axis G to the inner peripheral portion of the ring member 97. First frictional resistance R1 between the connection member 85 of the driving body 88 and the ring member 97 is smaller than second frictional resistance R2 between the ring member 97 and the proximal support portion 102 of the cavity defining portion 68 (channel defining portion 70).

As shown in FIG. 6, in the channel defining portion 70, a second channel diameter setting portion 106 is provided to the proximal direction side of the first channel diameter setting portion 105. The second channel diameter setting portion 106 is extended through the connection pipe 69 and the member channel tube 71 from the cavity defining portion 68 toward the proximal direction. That is, the second channel diameter setting portion 106 is extended from the cavity defining portion 68 up to the member insertion portion 75. In the second channel diameter setting portion 106, the channel diameter dimension from the driving axis G is a second channel diameter dimension D2 which is larger than the first channel diameter dimension D1. Therefore, the second channel diameter dimension D2 in the second channel diameter setting portion 106 is larger than the driving unit diameter dimension D0 in the proximal supported portion 101.

In the cavity defining portion 68 (channel defining portion 70), a channel diameter changing portion 107 is provided between the first channel diameter setting portion 105 and the second channel diameter setting portion 106. In the channel diameter changing portion 107, a channel diameter dimension from the driving axis G is increased as in goes toward the proximal direction. In the channel diameter changing portion 107, a channel diameter dimension is increased from the first channel diameter dimension D1 to the second channel diameter dimension D2. The proximal supported portion 101 of the driving unit 80 is guided to the proximal support portion 102 of the cavity defining portion 68 (channel defining portion 70) by the channel diameter changing portion 107. That is, the channel diameter changing portion 107 is a proximal guide portion which can (configured to) guide the driving unit 80 so that the proximal supported portion 101 is supported by the proximal support portion 102.

Now, the function of the endoscope device 1 according to the present embodiment is described. The insertion section 2 to which the rotating tubular member 65 and the tube member 30 are attached is inserted into a body. When the rotating tubular member 65 and the tube member 30 are rotated relative to the insertion section 2 in one of the directions around the longitudinal axis, the motor 77 is driven by the operation in the driving operation input section 15. As a result, the driving unit 80 is driven, and the driving unit 80 rotates in one of the directions around the driving axis. If the gear portion 83 of the driving unit 80 rotates around the driving axis G, the rotation driving force is transmitted to the inner peripheral gear portion 89, and the rotating tubular member 65 and the tube member 30 rotate together relative to the insertion section 2 in one of the directions around the longitudinal axis.

In this case, the driving unit 80 is supported by the distal supported portion 91 located to the distal direction side of the gear portion 83 and by the proximal supported portion 101 located to the proximal direction side of the gear portion 83. As a result, the driving unit 80 is supported by the distal support portion 92 and the proximal support portion 102 so that the driving axis G is parallel to the longitudinal axis C in the gear portion 83. As the driving axis G of the driving unit 80 is parallel to the longitudinal axis C in the gear portion 83, the gear portion 83 of the driving unit 80 rotatable in the directions around the driving axis is properly toothed with the inner peripheral gear portion 89 of the rotating tubular member 65 rotatable in the directions around the longitudinal axis. That is, the inner peripheral gear portion 89 which is the driving force receiving portion is properly connected to the gear portion 83 of the driving unit 80, and the rotation driving force to rotate the rotating tubular member 65 is properly transmitted to the inner peripheral gear portion 89 of the rotating tubular member 65. This ensures the performance of the rotation of the rotating tubular member 65 relative to the insertion section 2.

The driving unit 80 includes the driving body 88 which rotates in one of the directions around the driving axis together with the gear portion 83, and a ring member 98 which is rotatable relative to the driving body 88 in the directions around the driving axis. The proximal supported portion 101 is provided on the outer peripheral portion of the ring member 97. Therefore, the proximal support portion 102 of the channel defining portion 70 is out of contact with the driving body 88 which rotates together with the gear portion 83. This effectively prevents wear (abrasion) caused by the contact between the channel defining portion 70 and the driving body 88, and improves the durability of the channel defining portion 70 and the driving body 88. The first frictional resistance R1 between the connection member 85 of the driving body 88 and the ring member 97 is smaller than the second frictional resistance R2 between the ring member 97 and the proximal support portion 102 of the cavity defining portion 68 (channel defining portion 70). This further improves the durability of the channel defining portion 70 and the driving body 88.

In the section perpendicular to the driving axis G which passes through the proximal supported portion 101 of the ring member 97 of the driving unit 80, the driving unit diameter dimension D0 from the driving axis G to the proximal supported portion 101 is the same as the first channel diameter dimension D1 in the first channel diameter setting portion 105 in which (to which) the proximal support portion 102 is provided. In the section perpendicular to the driving axis G, the first member diameter dimension T1 from the driving axis G to the outer peripheral portion of the connection member 85 of the driving body 88 is substantially the same as the second member diameter dimension T2 from the driving axis G to the inner peripheral portion of the ring member 97. This ensures that the driving axis G is kept parallel to the longitudinal axis C in the gear portion 83 even when the proximal supported portion 101 is provided in the ring member 97 which does not rotate together with the gear portion 83.

When the gear portion 83 of the driving gear 82 is disposed in the gear placement cavity 67, the driving unit 80 is inserted into the member channel 72 from the member insertion portion 75. The driving unit 80 is then moved through the member channel 72 toward the distal direction until the distal supported portion 91 is supported by the distal support portion 92 and the proximal supported portion 101 is supported by the proximal support portion 102.

Here, the cavity defining portion 68 (channel defining portion 70) of the base member 57 is provided with the insertion section side taper surface 93 in which the dimension from the driving axis G in the section perpendicular to the driving axis G is increased as it goes toward the proximal direction. The columnar member 87 of the driving unit 80 is provided with the driving side taper surface 95 in which the dimension from the driving axis G in the section perpendicular to the driving axis G is increased as it goes toward the proximal direction. Thus, when the gear portion 83 is disposed in the gear placement cavity 67, the distal supported portion 91 of the driving unit 80 is guided to the distal support portion 92 of the cavity defining portion 68 (channel defining portion 70) by the insertion section side taper surface 93. Therefore, when the gear portion 83 is disposed in the gear placement cavity 67, the driving unit 80 can be easily guided so that the distal supported portion 91 is supported by the distal support portion 92.

FIG. 7 is a diagram showing a state in which the proximal supported portion 101 of the driving unit 80 passes through the second channel diameter setting portion 106 of the channel defining portion 70 during the movement of the driving unit 80 through the member channel 72. As described above, in the channel defining portion 70, the second channel diameter setting portion 106 is provided to the proximal direction side of the first channel diameter setting portion 105. The second channel diameter dimension D2 in the second channel diameter setting portion 106 is larger than the first channel diameter dimension D1 in the first channel diameter setting portion 105 and the driving unit diameter dimension D0 in the proximal supported portion 101. Therefore, as shown in FIG. 7, the proximal supported portion 101 does not easily contact the second channel diameter setting portion 106 during the movement of the driving unit 80 through the member channel 72. Thus, the driving unit 80 can be easily moved through an inside of the second channel diameter setting portion 106.

The second channel diameter setting portion 106 is extended from the member insertion portion 75 which is the proximal end of the member channel 72. Therefore, when the gear portion 83 is disposed in the gear placement cavity 67, the driving unit 80 can be easily moved toward the distal direction until the proximal supported portion 101 of the driving unit 80 is located at a distal end of the second channel diameter setting portion 106.

The channel diameter changing portion 107 is provided between the first channel diameter setting portion 105 and the second channel diameter setting portion 106. In the channel diameter changing portion 107, the channel diameter dimension from the driving axis G is increased as it goes toward the proximal direction. Thus, when the gear portion 83 is disposed in the gear placement cavity 67, the proximal supported portion 101 of the driving unit 80 is guided to the proximal support portion 102 of the cavity defining portion 68 (channel defining portion 70) by the channel diameter changing portion 107. Therefore, when the gear portion 83 is disposed in the gear placement cavity 67, the driving unit 80 can be easily guided so that the proximal supported portion 101 is supported by the proximal support portion 102.

When the member channel 72 and the driving unit 80 are cleaned, the driving unit 80 is removed from the member insertion portion 75, and a cleaning liquid is then poured into the member channel 72. The member channel 72 is cleaned with the cleaning liquid. The driving unit 80 removed from the member channel 72 is also cleaned with the cleaning liquid. In this case, since the driving unit 80 is cleaned after removed from the member channel 72, the driving unit 80 can be easily cleaned. The outflow of the cleaning liquid to an outside of the member channel 72 from parts other than the member insertion portion 75 and the opening 73 is prevented. This effectively prevents the adhesion of the cleaning liquid to the imaging cable 41 and the light guide 42 provided to the inside of the insertion section 2.

Accordingly, the endoscope device 1 having the configuration described above has the following advantageous effects. That is, in the endoscope device 1, the driving unit 80 is supported by the distal supported portion 91 located to the distal direction side of the gear portion 83 and by the proximal supported portion 101 located to the proximal direction side of the gear portion 83. As a result, the driving unit 80 is supported by the distal support portion 92 and the proximal support portion 102 so that the driving axis G is parallel to the longitudinal axis C in the gear portion 83. As the driving axis G of the driving unit 80 is parallel to the longitudinal axis C in the gear portion 83, the gear portion 83 of the driving unit 80 rotatable in the directions around the driving axis is properly toothed with the inner peripheral gear portion 89 of the rotating tubular member 65 rotatable in the directions around the longitudinal axis. That is, the inner peripheral gear portion 89 which is the driving force receiving portion is properly connected to the gear portion 83 of the driving unit 80, and the rotation driving force to rotate the rotating tubular member 65 can be properly transmitted to the inner peripheral gear portion 89 of the rotating tubular member 65. This can ensure the performance of the rotation of the rotating tubular member 65 relative to the insertion section 2.

Modifications

In the first embodiment, the insertion section side taper surface 93, which is provided from the distal support portion 92 toward the proximal direction and in which the dimension from the driving axis G in the section perpendicular to the driving axis G is increased as it goes toward the proximal direction, is the distal guide portion. However, the present invention is not limited to this. For example, as in a first modification shown in FIG. 8, an insertion section side taper surface 111 may be provided from the distal support portion 92 toward the distal direction in the cavity defining portion 68 (channel defining portion 70). In the insertion portion side taper surface 111, a dimension from the driving axis G in the section perpendicular to the driving axis G is increased as it goes toward the distal direction. In the present modification as well, the driving axis G of the driving unit 80 passes through the distal supported portion 91 and the distal support portion 92, as in the first embodiment.

Furthermore, in the present modification, a driving side taper surface 112 is provided to the columnar member 87 of the driving unit 80 from the distal supported portion 91 toward the distal direction. In the driving side taper surface 112, a dimension from the driving axis G in the section perpendicular to the driving axis G is increased as it goes toward the distal direction. In such a configuration, the distal supported portion 91 of the driving unit 80 is guided to the distal support portion 92 of the cavity defining portion 68 (channel defining portion 70) by the insertion section side taper surface 111. That is, the insertion section side taper surface 111 is a distal guide portion which can (configured to) guide the driving unit 80 so that the distal supported portion 91 is supported by the distal support portion 92.

In consequence, it is appreciated from the first modification that the channel defining portion 70 (cavity defining portion 68) has only to be provided with the distal guide portion (93; 111) which can (configured to) guide the driving unit 80 so that the distal supported portion 91 is supported by the distal support portion 92.

Figure 9B:
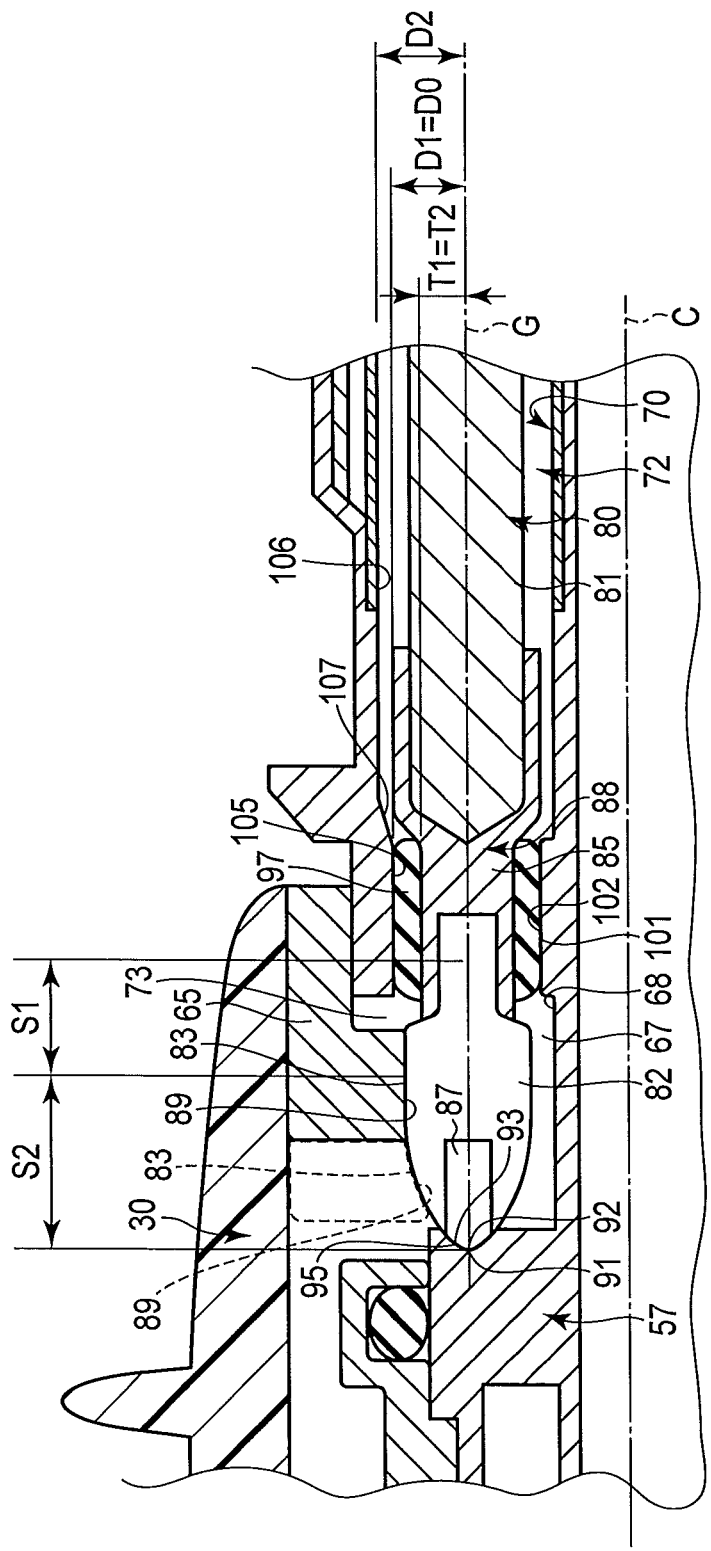
FIG. 9B is a schematic sectional view showing the configuration of a part of a second intermediary connection section in the vicinity of a gear placement cavity according to a third modification.

Although the proximal supported portion 101 is provided to (in) the ring member 97 rotatable relative to the driving body 88 in the directions around the driving axis in the first embodiment, the present invention is not limited to this. For example, as in a second modification shown in FIG. 9A, the proximal supported portion 101 may be provided on the outer peripheral portion of the connection member 85 of the driving body 88. In the present modification, the ring member 97 is not provided. Therefore, the whole driving unit 80 is the driving body 88 rotatable in the directions around the driving axis together with the gear portion 83. The proximal supported portion 101 is located on the outer peripheral portion of the driving body 88, and is thus located on the outer peripheral portion of the driving unit 80.

In the present modification as well, the channel defining portion 70 includes the first channel diameter setting portion 105, the second channel diameter setting portion 106, and the channel diameter changing portion 107, and the proximal support portion 102 is located in the first channel diameter setting portion 105, as in the first embodiment. In the section perpendicular to the driving axis G which passes through the proximal supported portion 101 of the connection member 85 of the driving unit 80, the driving unit 80 has the driving unit diameter dimension D0 from the driving axis G to the proximal supported portion 101. In the present modification as well, the driving unit diameter dimension D0 is the same as the first channel diameter dimension D1 in the first channel diameter setting portion 105, as in the first embodiment. The second channel diameter dimension D2 in the second channel diameter setting portion 106 is larger than the driving unit diameter dimension D0 in the proximal supported portion 101. Thus, the proximal supported portion 101 of the driving unit 80 is guided to the proximal support portion 102 of the cavity defining portion 68 (channel defining portion 70) by the channel diameter changing portion 107.

In consequence, it is appreciated from the second modification that the channel defining portion 70 (cavity defining portion 68) has only to be provided with the proximal guide portion (107) which can guide the driving unit 80 so that the proximal supported portion 101 is supported by the proximal support portion 102.

The gear portion 83 of the driving gear 82 and the inner peripheral gear portion 89 of the rotating tubular member 65 have only to be toothed with each other between the distal support portion 92 and the proximal support portion 102 in directions parallel to the driving axis G. For example, as in a third modification shown in FIG. 9B, the position where the gear portion 83 is toothed with the inner peripheral gear portion 89 may be located to the proximal side with respect to the tooth position in the first embodiment (the position indicated by a dotted line in FIG. 9B). That is, in the present modification, the position where the gear portion 83 is toothed with the inner peripheral gear portion 89 is closer to the proximal support portion 102 than in the first embodiment. As a result, in the directions parallel to the driving axis G, a first distance S1 between the tooth position and the proximal support portion 102 is smaller than a second distance S2 between the tooth position and the distal support portion 92. The proximal support portion 102 has a greater force to support the driving unit 80 than that of the distal support portion 92. Therefore, since the position where the gear portion 83 is toothed with the inner peripheral gear portion 89 is closer to the proximal support portion 102, the driving unit 80 (driving gear 82) is more stably supported. This further ensures that the driving axis G of the driving unit 80 is parallel to the longitudinal axis C in the gear portion 83, and the gear portion 83 of the driving unit 80 is more properly toothed with the inner peripheral gear portion 89 of the rotating tubular member 65 in the tooth position. This further ensures the performance of the rotation of the rotating tubular member 65 relative to the insertion section 2.

Although the base portion to which the rotating tubular member 65 is rotatably attached is formed by the single base member 57 in the first embodiment, the present invention is not limited to this. For example, the base portion may include two base members coupled to each other. That is, the insertion section 2 has only to be provided with a base portion to which the rotating tubular member 65 is rotatably attached.

Although the insertion device is the endoscope device 1 in the first embodiment, the present invention is not limited to this. For example, in a manipulator device which is the insertion device, the rotating tubular member 65 may be attached to a manipulator insertion section. That is, the insertion device has only to include an insertion section extended along the longitudinal axis C, and the insertion section has only to be an insertion section which is configured to be inserted into, for example, a body cavity.

It is appreciated from the above that the driving unit 80 has only to include the distal supported portion 91 located to the distal direction side of the gear portion 83, and the proximal supported portion 101 located to the proximal direction side of the gear portion 83. The channel defining portion 70 has only to be provided with the distal support portion 92 which is configured to support the distal supported portion 91 of the driving unit 80, and the proximal support portion 102 which is configured to support the proximal supported portion 101 of the driving unit 80. The driving unit 80 has only to be supported by a support unit including the distal support portion 92 and the proximal support portion 102 so that the driving axis G is parallel to the longitudinal axis C in the gear portion 83.

Referential Example

Figure 10:
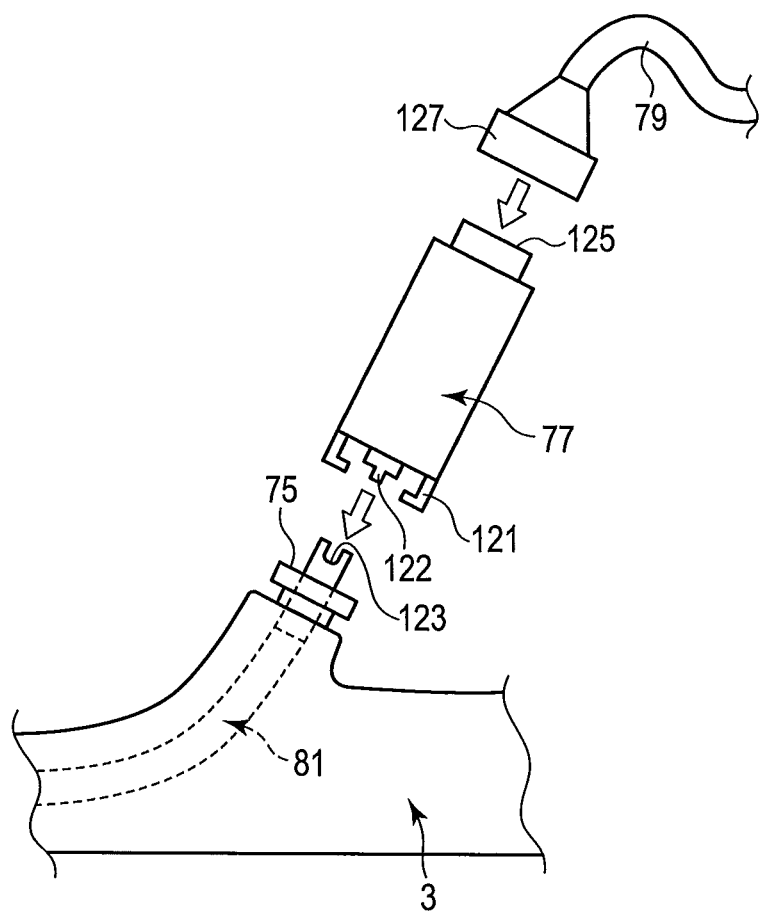
FIG. 10 is a schematic diagram showing the configuration of a member insertion portion of an operation section and a motor according to a referential example.

A referential example is described below with reference to FIG. 10 and FIG. 11. As shown in FIG. 10, the motor 77 which is a driving member includes a claw 121. When the claw 121 is locked with the member insertion portion 75, the motor 77 is attached to the member insertion portion 75. The motor 77 is also provided with an engagement protrusion 122. An engagement slot 123 which can be engaged with the engagement protrusion 122 is provided at a proximal end of the driving shaft 81. When the engagement protrusion 122 is engaged with the engagement slot 123, the motor 77 is connected to the driving shaft 81.

The motor 77 is also provided with a cable connection portion 125. A connector 127 is provided at one end of the motor cable 79. When the connector 127 is attached to the cable connection portion 125, the motor cable 79 is connected to the motor 77. When the driving unit 80 is driven, a driving current is supplied to the motor 77 from the driving control section 13 via the motor cable 79 in a state that the motor cable 79 is connected to the motor 77. As a result, the motor 77 is driven, and the driving unit 80 is driven.

Figure 11:
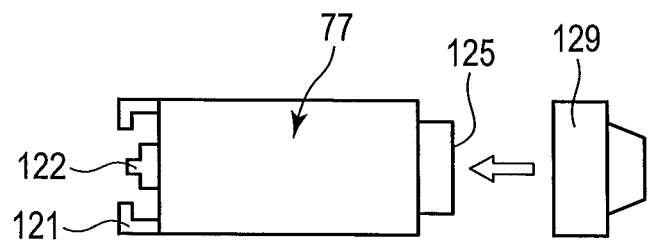
FIG. 11 is a schematic diagram showing the configuration of the motor and a waterproof cap according to the referential example.

When the motor 77 is cleaned, the connector 127 is removed from the cable connection portion 125, as shown in FIG. 11. Thus, the motor cable 79 is removed from the motor 77. A waterproof cap 129 is then attached to the cable connection portion 125. As a result, the motor 77 can be cleaned in a state that the motor 77 is attached to the member insertion portion 75, and the motor 77 can be cleaned together with the insertion section 2 and the operation section 3.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
an insertion section extended along a longitudinal axis;
a rotating tubular member which is attached to the insertion section so that the insertion section is inserted through the rotating tubular member, and which is rotatable relative to the insertion section in directions around the longitudinal axis;
a driving motor which is configured to cause a driving force to rotate the rotating tubular member;
a driving shaft, one end of which is connected to the driving motor and which is extended inside the insertion section, the driving shaft being configured to transmit the driving force caused in the driving motor;
a driving gear to which an other end of the driving shaft is coupled and which is configured to rotate when the driving force is transmitted through the driving shaft, the driving gear being configured to rotate so as to rotate the rotating tubular member;
a connection member which connects the driving shaft to the driving gear and which is configured to transmit the driving force from the driving shaft to the driving gear;
a ring member which is provided on an outer peripheral portion of the connection member and which is rotatable relative to the connection member;
a channel defining portion which defines a channel inside the insertion section, the driving gear, the connection member with the ring member and the driving shaft being configured to be disposed in the channel in this order from a distal direction side; and
a first channel diameter setting portion which is provided to the channel defining portion and in which an inner peripheral surface of the channel defining portion is protruded, the first channel diameter setting portion being configured to hold an outer peripheral surface of the ring member so as to support the connection member.

2. The insertion device according to claim 1, wherein the channel defining portion includes
   a second channel diameter setting portion which is provided to a proximal direction side of the first channel diameter setting portion, and which has a second channel diameter dimension larger than a first channel diameter dimension of the first channel diameter setting portion, and
   a channel diameter changing portion which is provided between the first channel diameter setting portion and the second channel diameter setting portion, and in which a channel diameter dimension is increased as it goes toward a proximal direction.

3. The insertion device according to claim 1, wherein a first frictional resistance between the connection member and the ring member is smaller than a second frictional resistance between the ring member and the first channel diameter setting portion.

4. The insertion device according to claim 1, further comprising:
   an insertion section side taper surface which is provided to a distal portion of the channel defining portion, and in which a dimension from a driving axis of the driving gear in a section perpendicular to the driving axis is increased in a range of all-around of the channel defining portion as it goes toward a proximal direction; and
   a columnar member which is provided to a distal portion of the driving gear, and which includes a driving side taper surface, a dimension from the driving axis in the driving side taper surface in the section perpendicular to the driving axis being increased in a range of all-around of the driving gear as it goes toward the proximal direction.

5. The insertion device according to claim 1, further comprising:
   an insertion section side taper surface which is provided to a distal portion of the channel defining portion, and in which a dimension from a driving axis of the driving gear in a section perpendicular to the driving axis is increased in a range of all-around of the channel defining portion as it goes toward the distal direction; and
   a columnar member which is provided to a distal portion of the driving gear, and which includes a driving side taper surface, in which a dimension from the driving axis in the driving side taper surface in the section perpendicular to the driving axis being increased in a range of all-around of the driving gear as it goes toward the distal direction.

6. The insertion device according to claim 1, further comprising a tube member which is attached to the rotating tubular member so that the insertion section is inserted through the tube member, and which is rotatable relative to the insertion section in the directions around the longitudinal axis together with the rotating tubular member,
   wherein the tube member includes a fin spirally extended along the longitudinal axis.

\* \* \* \* \*